United States Patent
Chau et al.

(10) Patent No.: US 7,183,373 B2
(45) Date of Patent: Feb. 27, 2007

(54) MNTF PEPTIDES AND COMPOSITIONS AND METHODS OF USE

(75) Inventors: Raymond Ming Wah Chau, Hong Kong (CN); Pui-Yuk Dorothy Ko, Monterey Park, CA (US)

(73) Assignee: Genervon Biopharmaceuticals LLC, Montebello, CA (US)

( * ) Notice: Subject to any disclaimer, the term of this patent is extended or adjusted under 35 U.S.C. 154(b) by 0 days.

(21) Appl. No.: 10/541,343

(22) PCT Filed: Jan. 21, 2004

(86) PCT No.: PCT/US2004/001468

§ 371 (c)(1),
(2), (4) Date: Jul. 5, 2005

(87) PCT Pub. No.: WO2004/065410

PCT Pub. Date: Aug. 5, 2004

(65) Prior Publication Data
US 2006/0052299 A1   Mar. 9, 2006

Related U.S. Application Data

(60) Provisional application No. 60/441,772, filed on Jan. 21, 2003.

(51) Int. Cl.
*A61K 38/00* (2006.01)
(52) U.S. Cl. ............... 530/300; 530/326; 530/327; 530/328; 530/329; 514/12
(58) Field of Classification Search ............ 514/12
See application file for complete search history.

(56) References Cited

U.S. PATENT DOCUMENTS 6,309,877 B1   10/2001   Chau
6,759,389 B1   7/2004    Chau
6,841,531 B2 *  1/2005   Chau ..................... 514/2

OTHER PUBLICATIONS

U.S. Appl. No. 10/858,545, filed Nov. 11, 2004, Chau.
U.S. Appl. No. 10/858,286, filed Dec. 2, 2004, Chau.
U.S. Appl. No. 10/858,543, filed Dec. 30, 2004, Chau.
Chau, R.M.W. et al:"Muscle neurotrophic factors specific for anterior horn motoneurons of rat spinal cord." Recent Advances in Cellular & Molecular Biology, vol. 5,1992, 89-94.
Zhou, Minghua et al; "Production and assessment of MAB specific for the 35kD MNTF from rat skeletal muscle." J. Monoclonal Antibody 1992. vol. 8(3), 40-44.
Yu, W.H.A. et al: "Muscle-derived Motoneuronotrophic factors promote survival of axontomized motoneurons on the facial nerve." Society for Neuroscience 22nd Ann.Mtg 1992, #546.
Chau, R. et al: "Synergetic effect of MNTF 1 & 2 on survival of axontomized motoneurons of sciatic nerve." 22nd Ann. Mtg. Of the Society for Neuroscience, 1992, vol. 18, #546.
Chau, R et al: "Effect of 22kD, 35kD molecules from skeletal muscle extract on ant. horn motoneuron of lumbar spine in rat." Chinese Science Bulletin, 1992, 37(2); 1742-1745.
Chau, R.M.W. et al,: "Cloning of genes from MNTF1 and its receptor by monoclonal antibody probes." Society for Neuroscience Abstracts, vol. 19, 1993, p. 252, #109.23.
Zhou, Minghua et al: "Changes in MNTF and its receptor in tongue muscle post-denervation of the hypoglossal nerve." Acta Anatomica Sinica, vol. 24, No. 4, Oct. 1993, 391-395.
Zhang, Nanling et al: "Immunohistochemical localization of muscle-derived motoneuronotrophic factor 1 & its receptor in the stomach of rat." Jiepou Xuebao (1994),25(1), 56-58.
Zhou, Ming-Hua (Chau, R.M.W.) et al: "Immunohistochemical localization of Motoneuronotrophic factor in fetal and neonatal rats." Jiepou Xuebao (1994), 25(2), 189-192.
\* Full text in Chinese, English translation for abstract only.
Chau, R.et al: "Effects of 22, 35 kD MNTF of axonal regeneration in peripheral nerve autografts in rat spinal cord." Chinese J. of Spine & Spinal Cord, 1995, 5(6): 248-252.
Chau, R.M.W. et al,: "Biological effect of MNTF on wobbler mice with motoneuron disease" 25th Annual Meeting of the Society for Neuroscience, vol. 22 No. 1-3, 1996, 233.
Zhou, Ming-Hua et al: "Distribution of MNTF1 in spinal cord and limb muscles of mice with motoneuron disease" Acta Academiae Medicinae Sinicae vol. 19, No. 3, Jun. 1997,171-178.
Di, Xinyu et al:"Immunohistochemical localization of c-fos, p53 protein & MNTF 1 receptor in early human placental villi." Jiepou Xuebao vol. 28, No. 4, 404-406, Oct. 1997.
Di, Xinyu et al: "Localization & morphometric study on MNTF 1 & its receptor in developing chronic villi of human placenta." Jiepou Xuebao, vol. 29 No. 1, 86-89, Jan. 1998.
Nussbaum, D., Brushart, T. et al: "Motoneuron Trophic Factor (MNTF) from gene to function." 2003 Society for Neuroscience Annual Meeting Poster #357.19.
\* Full text in Chinese, English translation for abstract only.

\* cited by examiner

*Primary Examiner*—Christopher R. Tate
*Assistant Examiner*—Maury Audet
(74) *Attorney, Agent, or Firm*—Duane Morris LLP

(57) ABSTRACT

The present invention is directed to novel peptides and compositions capable of modulating viability and growth in neuronal cells, and to methods of modulating neuronal cell viability and growth employing the novel peptides and compositions of the invention. In one aspect, the invention is directed to novel peptide analogues of motoneuronotrophic factor 1 containing either a "WMLSAFS" or "FSRYAR domain," which is sufficient for neurotrophic or neurotropic function.

9 Claims, 5 Drawing Sheets

| | | |
|---|---|---|
| SEQ ID NO:1 | 33-mer | LGTFWGDTLNCWMLSAFSRYARCLAEGHDGPTQ |
| SEQ ID NO:2 | 6-mer | FSRYAR |
| SEQ ID NO:3 | 7-mer | WMLSAFS |
| SEQ ID NO:4 | 10-mer | MLSAFSRYAR |
| SEQ ID NO:5 | 11-mer | FSRYARCLAEG |
| SEQ ID NO:6 | 13-mer | CWMLSAFSRYARC |
| SEQ ID NO:7 | 21-mer | MLSAFSRYARCLAEGHDGPTQ |

FIG. 1

SEQUENCE LISTING

<160> NUMBER OF SEQ ID NOS: 7

<210> SEQ ID NO 1
<211> LENGTH: 33
<212> TYPE: PRT
<213> ORGANISM: Artificial
<220> FEATURE:
<223> OTHER INFORMATION: Synthetic peptide

<400> SEQUENCE: 1

Leu Gly Thr Phe Trp Gly Asp Thr Leu Asn Cys Trp Met Leu Ser Ala
1               5                   10                  15

Phe Ser Arg Tyr Ala Arg Cys Leu Ala Glu Gly His Asp Gly Pro Thr
            20                  25                  30

Gln

<210> SEQ ID NO 2
<211> LENGTH: 6
<212> TYPE: PRT
<213> ORGANISM: Artificial
<220> FEATURE:
<223> OTHER INFORMATION: Synthethic peptide

<400> SEQUENCE: 2

Phe Ser Arg Tyr Ala Arg
1               5

<210> SEQ ID NO 3
<211> LENGTH: 7
<212> TYPE: PRT
<213> ORGANISM: Artificial
<220> FEATURE:
<223> OTHER INFORMATION: Synthetic peptide

<400> SEQUENCE: 3

Trp Met Leu Ser Ala Phe Ser
1               5

<210> SEQ ID NO 4
<211> LENGTH: 10
<212> TYPE: PRT
<213> ORGANISM: Artificial
<220> FEATURE:
<223> OTHER INFORMATION: Synthetic peptide

<400> SEQUENCE: 4

Met Leu Ser Ala Phe Ser Arg Tyr Ala Arg
1               5                   10

<210> SEQ ID NO 5
<211> LENGTH: 11
<212> TYPE: PRT
<213> ORGANISM: Artificial
<220> FEATURE:
<223> OTHER INFORMATION: Synthetic peptide

<400> SEQUENCE: 5

Phe Ser Arg Tyr Ala Arg Cys Leu Ala Glu Gly
1               5                   10

<210> SEQ ID NO 6
<211> LENGTH: 13
<212> TYPE: PRT
<213> ORGANISM: Artificial

-continued

```
<220> FEATURE:
<223> OTHER INFORMATION: Synthetic peptide

<400> SEQUENCE: 6

Cys Trp Met Leu Ser Ala Phe Ser Arg Tyr Ala Arg Cys
1               5                   10

<210> SEQ ID NO 7
<211> LENGTH: 21
<212> TYPE: PRT
<213> ORGANISM: Artificial
<220> FEATURE:
<223> OTHER INFORMATION: Synthetic peptide

<400> SEQUENCE: 7

Met Leu Ser Ala Phe Ser Arg Tyr Ala Arg Cys Leu Ala Glu Gly His
1               5                   10                  15

Asp Gly Pro Thr Gln
            20
```

MNTF PEPTIDES AND COMPOSITIONS AND METHODS OF USE

RELATED APPLICATIONS

The present application claims the benefit of U.S. provisional application No. 60/441,772 filed Jan. 21, 2003, which is incorporated herein by reference in its entirety.

BACKGROUND

Neuronotrophic factors (NTFs) are a specialized group of proteins which function to promote the survival, growth, maintenance, and functional capabilities of selected populations of neurons. Recent studies have demonstrated that neuronal death occurs in the nervous systems of vertebrates during certain periods of growth and development. However, the addition of soluble neuronal trophic factors from associated target tissues serves to mitigate this phenomenon of neuronal death. The following citations discuss neuronal trophic factors and their disclosures are hereby incorporated by reference: Chau, R. M. W., et al., Neuronotrophic Factor, 6 *Chin. J Neuroanatomy* 129 (1990); Kuno, M., Target Dependence of Motoneuronal Survival: The Current Status, 9 *Neurosci. Res.* 155 (1990); Bard, Y. A., Trophic Factors and Neuronal Survival, 2 *Neuron* 1525 (1989); Oppenheim, R. W., The Neurotrophic Theory and Naturally Occurring Motoneuron Death, 12 *TINS* 252 (1989); Bard, Y. A., What, If Anything, is a Neurotrophic Factor?, 11 *TINS* 343 (1988); and Thoenen, H., and Edgar, D., Neurotrophic Factors, 229 *Science* 238 (1985).

In the vertebrate neuromuscular system, the survival of embryonic motoneurons have been found to be dependent upon specific trophic substances derived from the associated developing skeletal muscles. Skeletal muscles have been shown, by both in vivo and in vitro studies, to produce substances which are capable of enhancing the survival and development of motoneurons by preventing the embryonic motoneurons from degeneration and subsequent, natural cellular death. See O'Brian, R. J. and Fischbach, G. D., Isolation of Embryonic Chick Motoneurons and Their Survival In Vitro, 6 *J. Neurosci.* 3265 (1986); Hollyday, M. and Hamburger, V., Reduction of the Naturally Occurring Motor Neuron Loss by Enlargement of the Periphery, 170 *J. Comp. Neurol.* 311 (1976), whose disclosures are incorporated herein by reference. Similarly, several investigators have reported that chick and rat skeletal muscles possess certain trophic factors which can prevent the natural cellular death of embryonic motoneurons both in vivo and in vitro. See McManaman, J. L., et al., Purification of a Skeletal Muscle Polypeptide Which Stimulates Choline Acetyltransferase Activity in Cultured Spinal Cord Neurons, 263 *J. Biol. Chem.* 5890 (1988); Oppenheim, R. W., et al., Reduction of Naturally Occurring Motoneuron Death In Vitro by a Target Derived Neurotrophic Factor, 240 *Science* 919 (1988); and Smith, R. G., et al., Selective Effects of Skeletal Muscle Extract Fractions on Motoneurons Development In Vivo, 6 *J. Neurosci.* 439 (1986), whose disclosures are incorporated herein by reference.

In addition, a polypeptide has been isolated from rat skeletal muscle which has been found to selectively enhance the survival of embryonic chick motoneurons in vivo, as well the activity of choline acetyltransferase in these motoneurons. This polypeptide has been named Choline Acetyltransferase Development Factor (CDF) and its biological function has been demonstrated to be different from other trophic factors such as Nerve Growth Factor (NGF), Ciliary Ganglion Neurotrophic Factor (CNTF), Brain-Derived Neurotrophic Factor (BDNF), and Retinal Ganglion Neurotrophic Factor (RGNTF). See Levi-Montalcini, R., "Developmental Neurobiology and the Natural History of Nerve Growth Factor," 5 *Ann. Rev. Neurosci.* 341 (1982); Varon, S., et al., Growth Factors. In: *Advances in Neurology*, Vol. 47: Functional Recovery in Neurological Disease, Waxman, S. G. (ed.), Raven Press, New York, pp. 493–521 (1988); Barde, Y. A., Trophic Factors and Neuronal Survival, 2 *Neuron* 1525 (1989); Chau, R. M. W., et al., The Effect of a 30 kD Protein from Tectal Extract of Rat on Cultured Retinal Neurons, 34 *Science in China*, Series B, 908 (1991), whose disclosures are incorporated herein by reference.

The isolation and characterization of two motoneuronotrophic factors from rat muscle tissue having apparent molecular weights of 35 kD and 22 kD were reported by Chau et al. See Chau, R. M. W., et al., Muscle Neuronotrophic Factors Specific for Anterior Horn Motoneurons of Rat Spinal Cord. In: *Recent Advances in Cellular and Molecular Biology*, Vol. 5, Peeters Press, Leuven, Belgium, pp. 89–94 (1992), the disclosure of which is hereby incorporated by reference. The 35 kD protein has been defined by Dr. Chau as motoneuronotrophic factor 1 (MNTF1) and the apparent 22 kD protein as motoneuronotrophic factor 2 (MNTF2). These two trophic factors have been demonstrated in vitro to support the growth and/or regeneration of both isolated anterior horn motoneurons and spinal explants of rat lumber spinal cord.

Subsequently, in 1993, Chau et al reported immunological screening of lambda gt11 clones from a human retinoblastoma cDNA library using a monoclonal antibody to MNTF1 as an immunoprobe. Immunoblots of extracts from an immunopositive clone stained an MNTF1 protein having an apparent molecular weight of 55 kD See Chau, R. M. W., et al., Cloning of Genes for Muscle-Derived Motoneuronotrophic Factor 1 (MNTF1) and Its Receptor by Monoclonal Antibody Probes, (abstract) 19 *Soc. for Neurosci.* part 1, 252 (1993), the disclosure of which is hereby incorporated by reference. An extract containing the cloned human MNTF1 was shown to have biological activity similar to that of the "native" MNTF1 protein in that it supported the in vitro growth of rat anterior horn motoneurons.

More recently, U.S. Pat. No. 6,309,877 disclosed a family of neuronotrophic factors which possess the ability to exert a trophic effect on motoneurons. The motoneurotrophic factors were isolated, nucleic acid sequences encoding these factors were cloned and expressed, and both the nucleic acid and polypeptide sequences were provided. In particular, recombinant proteins MNTF1–F3 and MNTF1–F6 encoded by 1443 and 972 base pair inserts, respectively, were expressed as either fusion proteins or purified fragments. The isolated factors and the expressed, recombinant factors, were capable of inducing the continued viability and neurite outgrowth of motoneurons. Therefore, these factors have been classified as "motoneuronotrophic factors" or "MNTFs."

The MNTF1–F6 clones reported in U.S. Pat. No. 6,309,877 encode a 33 amino acid fragment of MNTF1. Recombinant protein containing this sequence reacted with monoclonal antibody to MNTF1, maintained motoneuron viability, increased neurite outgrowth, reduced cell death/apoptosis and supported the growth and "spreading" of motoneurons into giant, active neurons with extended growth cone-containing axons. Consequently, the following studies were conducted to determine if a peptide comprising a "minimal" active site can be synthesized, which still retains the biological activity of this MNTF1 fragment.

SUMMARY OF THE INVENTION

The present invention is directed to novel peptides and compositions containing portions of the MNTF-molecule that are useful for modulating the viability and proliferation of neuronal cells, thereby providing for neurotrophic peptides that can be readily synthesized.

In particular, the present invention is directed to a novel protein domain of general significance to the actions of motoneuronotrophic factors, which has been identified and mapped to two short overlapping subsequences in the MNTF1 molecule. These heretofore unrecognized protein domains, which is designated herein the "WMLSAFS" and "FSRYAR" domains, are sufficient to modulate the viability and proliferation of neuronal cells. Moreover, truncated MNTF1 species encompassing these domain are themselves sufficient to stimulate the growth of motoneuron/neuroblastoma cell hybrids in cell proliferation assays.

In one aspect, then, the invention is directed to purified and isolated MNTF peptide analogues comprising the WMLSAFS (SEQ ID NO: 3) or FSRYAR (SEQ ID NO: 2) domains and to molecules that mimic its structure and/or function, useful for inducing or modulating the viability and growth of a neuronal cell. 1. Particular embodiments of such MNTF peptide analogues are disclosed herein as SEQ ID NO:2, SEQ ID NO:3, SEQ ID NO:4, SEQ ID NO:5, SEQ ID NO:6, and SEQ ID NO:7.

The present invention also relates to compositions and methods for modulating the viability and/or growth of a neuronal cells by administering the MNTF peptide analogues in vitro to cell cultures or in vivo to an individual suffering from a nerve injury or neurodegenerative disorder, in order to promote cell proliferation or stabilize inappropriate cell death, and/or in either case to restore normal cell behavior. The present invention is also directed to the use of MNTF peptide analogues for its antiproliferative effects on non-neuronal cells, particularly its use as an antifibrotic or anti-inflammatory agent in wound healing

BRIEF DESCRIPTION OF THE DRAWINGS

These and other features, aspects, and advantages of the present invention will become better understood with regard to the following description and accompanying drawings, where:

FIG. 1 shows amino acid sequences of various MNTF1 peptides;

DETAILED DESCRIPTION

Figure 2:
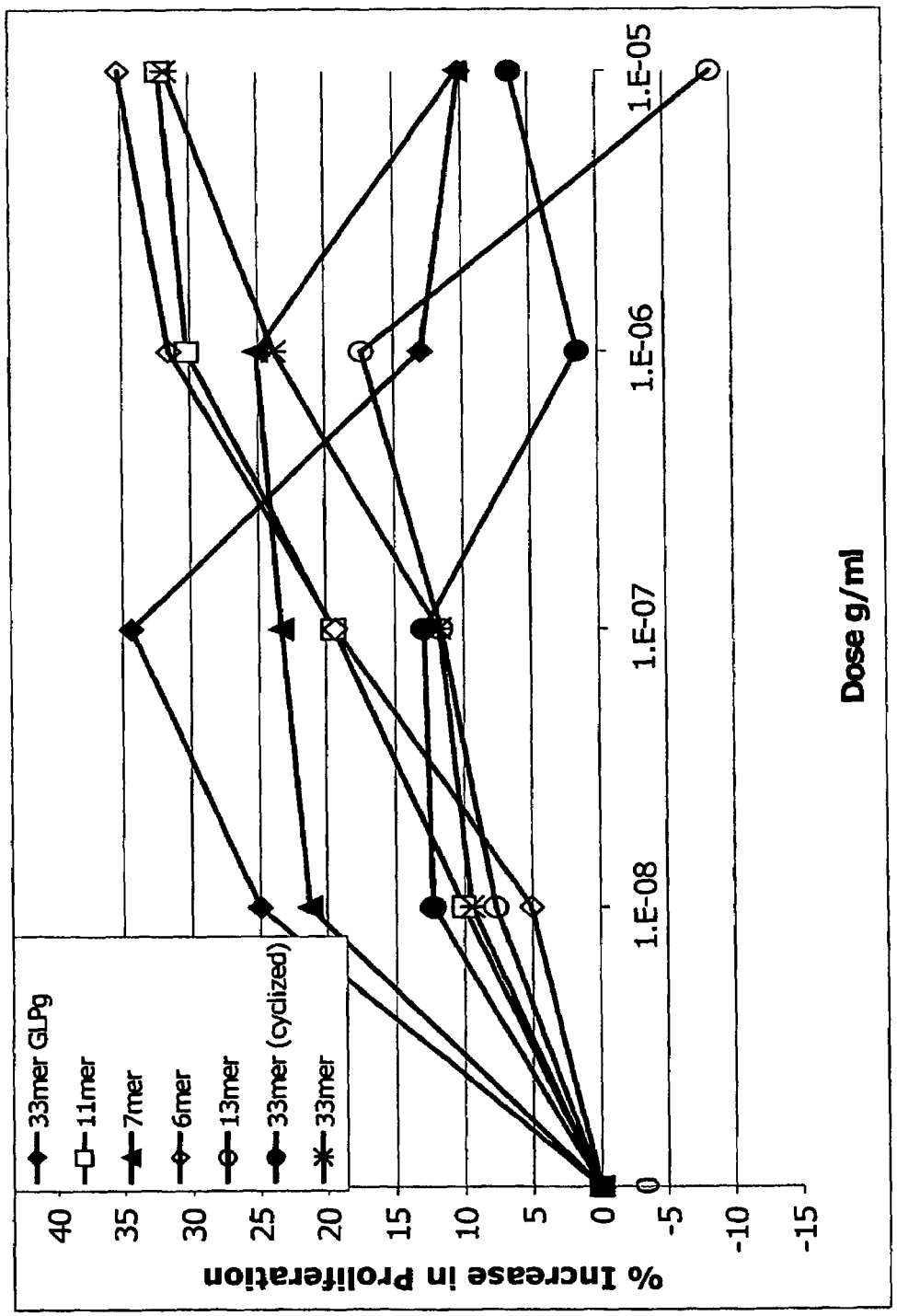
FIG. 2 shows percent increases in proliferation of VSC4.1 cells by MNTF1–F6 33mer and its peptide derivatives at various doses.

Technical and scientific terms used herein have the meanings commonly understood by one of ordinary skill in the art to which the present invention pertains, unless otherwise defined. Reference is made herein to various methodologies known to those of skill in the art. Publications and other materials setting forth such known methodologies to which reference is made are incorporated herein by reference in their entireties as though set forth in full. Standard reference works setting forth the general principles of recombinant DNA technology include Sambrook, J., et al., Molecular Cloning: A Laboratory Manual, 2d Ed., Cold Spring Harbor Laboratory Press, Planview, N.Y. (1989); McPherson, M. J., Ed., Directed Mutagenesis: A Practical Approach, IRL Press, Oxford (1991); Jones, J., Amino Acid and Peptide Synthesis, Oxford Science Publications, Oxford (1992); Austen, B. M. and Westwood, O. M. R., Protein Targeting and Secretion, IRL Press, Oxford (1991). Any suitable materials and/or methods known to those of skill can be utilized in carrying out the present invention; however, preferred materials and/or methods are described herein.

Overview

The isolation and characterization of two mononeuronotrophic factors (MNTF1 and MNTF2) from rat muscle tissues as well as the subsequent cloning of a recombinant MNTF1–F6 gene derived from a human retinoblastoma cDNA library, is described in U.S. Pat. No. 6,309,877 (as well as co-pending U.S. patent application Ser. Nos. 09/989,481, 08/928,862, filed Sep. 12, 1997, Ser. No. 08/751,225, filed Nov. 15, 1996, and U.S. provisional patent application 60/026,792, filed on Sep. 27, 1996; all of which are hereby incorporated by reference in their entirety). The MNTF1–F6 gene sequence encodes a 33 amino acid sequence referred to herein as SEQ ID NO:1.

The naturally occurring and recombinant MNTF1 polypeptides were shown to selectively enhance the survival in vitro of anterior horn motor neurons isolated from rat lumbar spinal cord explants. Photomicrographs of treated cultures exhibited neurite outgrowth of myelinated nerve fibers and a marked reduction in the growth of non-neuronal cells, e.g. glial cells and fibroblasts. Similarly, in vivo administration of MNTF1 to surgically axotomized rat peripheral nerves resulted in a markedly higher percentage of surviving motor neurons than untreated controls, which could be blocked by co-administration of anti-MNTF1 monoclonal antibody.

Further beneficial effects of MNTF1 were demonstrated in rats subjected to spinal cord hemi-section, repaired by a peripheral nerve autograft and implanted with MNTF1-containing gel sections in close proximity to the nerve graft junctions with spinal cord. MNTF1 treated animals exhibited greater numbers of surviving motor neurons, improved recovery of motor and sensory function, reduced inflammatory response (fewer infiltrating macrophages and lymphocytes), reduced collagen-containing scar tissue formation at the site of the graft, normal Schwann cell morphology and normal myelinated and non-myelinated nerve fiber formation.

The efficacy of MNTF in the treatment of neurogenerative disease was also demonstrated in the wobbler mouse animal model. Wobbler mice carry an autosomal double-recessive gene mutation that leads to the progressive degeneration of spinal and brain stem motor neurons. Approximately three weeks post partum, wobbler mice begin to develop the "wobbling" symptomology (Stage 1) with concomitant degeneration of cervical motor neurons leading to both the wasting of the muscle of the forelimbs and an inability to extend the digits and claws. By three months of age the pathologic symptomology progresses to stage 4, with a "clumping together" of all associated joints in the forelimbs, e.g., the wrist, elbow and shoulder joints, as well as an extensive loss of body weight and chronic fatigue. However, most wobbler mice die prior to reaching three months of age. Implantation of MNTF1-containing gel sections between the trapezius and rhomboid muscles and the C7-T3 region of the spinal cord delayed the progression of symptoms in wobbler mice, resulting in a general improvement in life span, health, respiration, body weight, strength of forelimbs as well as reduced vacuolation and chromatolysis of their cervical motor neurons compared to the control group.

Two previously unrecognized overlapping domains within the MNTF1–F6 molecule that appear to be sufficient for the known biological activities of MNTF1 have now been identified. Each of these domains, designated herein as the "WMLSAFS" and "FSRYAR" domains, are sufficient to stimulate the proliferation of motor neuron derived cell lines in a manner similar to the MNTF1–F6 33-mer. Similarly, the "FSRYAR" domain is sufficient to direct selective reinnervation of muscle targets by motor neurons in vivo in a manner similar to the MNTF1–F6 33-mer. In addition, the "FSRYAR" domain provides an antigenic epitope sufficient to raise antibody that recognizes any MNTF peptide containing the "FSRYAR" sequence, including the MNTF1–F6 33-mer.

As those of skill familiar with the art and the present invention will appreciate, sequences comprising the WMLSAFS and/or FSRYAR domain(s) provide MNTF peptide analogues for use in selectively modulating the viability and morphology of neuronal cells versus non-neuronal cells in vitro and in vivo. Moreover, compounds and compositions, which are capable of binding to the WMLSAFS and/or FSRYAR domain(s), provide agents for use in the detection and/or modulation of MNTF1 activity in target cells and tissues.

Peptides

As used herein, the term "WMLSAFS domain" or "FSRYAR domain" refers to a polypeptide domain demonstrated herein to be sufficient for the selective maintenance and axonal regeneration of neuronal cells, and to peptides and/or molecules capable of mimicking their structure and/or function. Preferred embodiments of the present invention comprise a peptide having the amino acid sequence: FSRYAR [SEQ ID NO:2] or WMLSAFS [SEQ ID NO:3], as well as functional equivalents thereof.

By "functional equivalent" is meant a peptide possessing a biological activity substantially similar to that of the WMLSAFS and/or FSRYAR domain(s), and is intended to include "fragments", "variants", "analogs", "homologs", or "chemical derivatives" possessing such activity or characteristic. Functional equivalents of the WMLSAFS and/or FSYAR domain(s), then, may not share an identical amino acid sequences, and conservative or non-conservative amino acid substitutions of conventional or unconventional amino acids are possible.

As used herein, the terms "biologically active peptide" and "biologically active fragment" refer to a peptide or polypeptide in accordance with the above description of motoneuronotrophic factors (MNTF) wherein the MNTF exhibits a protective effect on motor neurons and/or a proliferative effect on motor neuron derived cell lines.

The sequence of amino acid residues in a protein or peptide comprising the MNTF peptide analogues of the present invention are designated herein either through the use of their commonly employed three-letter designations or by their single-letter designations. A listing of these three-letter and one-letter designations may be found in textbooks such as Biochemistry, Second Edition, Lehninger, A., Worth Publishers, New York, N.Y. (1975). When the amino acid sequence is listed horizontally, the amino terminus is intended to be on the left end whereas the carboxy terminus is intended to be at the right end.

Reference herein to "conservative" amino acid substitution is intended to mean the interchangeability of amino acid residues having similar side chains. For example, glycine, alanine, valine, leucine and isoleucine make up a group of amino acids having aliphatic side chains; serine and threonine are amino acids having aliphatic-hydroxyl side chains; asparagine and glutamine are amino acids having amide-containing side chains; phenylalanine, tyrosine and tryptophan are amino acids having aromatic side chains; lysine, arginine and histidine are amino acids having basic side chains; and cysteine and methionine are amino acids having sulfur-containing side chains. Interchanging one amino acid from a given group with another amino acid from that same group would be considered a conservative substitution. Preferred conservative substitution groups include asparagine-glutamine, alanine-valine, lysine-arginine, phenylalanine-tyrosine and valine-leucine-isoleucine.

It will be appreciated by those of skill that the precise chemical structure of peptides comprising the various MNTF peptide analogues will vary depending upon a number of factors. For example, a given polypeptide may be obtained as an acidic or basic salt, or in neutral form, since ionizable carboxyl and amino groups are found in the molecule. For the purposes of the invention, then, any form of the peptides comprising the WMLSAFS and/or FSRYAR domain(s), which retain the biological activity of the MNTF1 33mer peptide is intended to be within the scope of the present invention.

MNTF1–F6 33-mer

In U.S. Pat. No. 6,309,877, there is provided a polypeptide (referred to therein as SEQ ID NO: 4) having the following amino acid sequence:

LGTFWGDTLNCWMLSA<u>FSRYAR</u>CLAEGHDGPTQ [SEQ ID NO:1]

Recombinant protein containing this sequence reacted with monoclonal antibody to MNTF-1, maintained motoneuron viability, increased neurite outgrowth, reduced motoneuron cell death/apoptosis and supported the growth and "spreading" of motoneurons into giant, active neurons with extended growth cone-containing axons. The MNTF1 33-mer, referred to herein as SEQ ID NO: 1, was synthesized by solid phase synthesis and served as positive control in cell proliferation assays, as described in the examples below. The linear 33-mer was found to be effective at increasing the proliferation of motoneuron/neuroblastoma cells, whereas a cyclized version of the peptide was less effective.

The present invention includes peptide analogues of MNTF1 that retain the ability of MNTF1 to promote the survival and maintenance of motor neurons. An MNTF peptide analogue in accordance with the present invention is typically 6 to 32 amino acids in length and contains at least one of two amino acid sequences, namely the WMLSAFS domain (SEQ ID NO:3) corresponding to amino acid residues 12 to 18 of SEQ ID NO:1, or the FSRYAR domain (SEQ ID NO:2) corresponding to amino acid residues 17 to 22 of SEQ ID NO:1. Preferred embodiments of the MNTF peptide analogue include a fragment of six to 32 consecutive amino acid residues of SEQ ID NO:1.

In alternative embodiments the amino sequence of the motoneuronotrophic factor peptide analogue is at least 70% identical to nine to 32 consecutive amino acid residues of SEQ ID NO: 1, at least 80% identical to eight to 32 consecutive amino acid residues of SEQ ID NO: 1 and most preferably, a least 90% identical to seven to 32 consecutive amino acid residues of SEQ ID NO: 1 as determined by BLAST analysis.

To compare a polypeptide sequence with the corresponding SEQ ID NO:1 fragment, a global alignment of the sequences can be performed using the BLAST programs publicly available through the National Center for Biotechnology Information (on the World Wide Web at ncbi.nlm.nih.gov). Prior to performing a global alignment, SEQ ID NO:1 can be submitted to GenBank. Default parameters provided by the National Center for Biotechnology Information can be used for a global alignment.

6-mer

In a particularly preferred embodiment, there is provided a peptide having the following amino acid sequence:
FSRYAR
Phe-Ser-Arg-Tyr-Ala-Arg [SEQ ID NO:2]

corresponding to amino acid residues 17–22 of SEQ ID NO:1, which was found to be sufficient to increase cell proliferation of motor neuron/neuroblastoma cells. This portion of the MNTF-1 molecule will be referred to hereinafter as the "FSRYAR" domain.

7-mer

In another preferred embodiment, there is provided a peptide having the following amino acid sequence:
WMLSAFS
Trp Met Leu Ser Ala Phe Ser [SEQ ID NO:3]

corresponding to amino acid residues 12–18 of SEQ ID NO:1. This 7 amino acid fragment of MNTF1 overlaps the FS residues of the FSRYAR domain. The peptide was also found to be a potent stimulator of motor neuron/neuroblastoma cells in vitro over a broad range of dosage levels. This portion of the MNTF-1 molecule will be referred to hereinafter as the "WMLSAFS" domain.

10-mer

In another preferred embodiment, there is provided a peptide having the following amino acid sequence:
MLSAFSRYAR
Met Leu Ser Ala Phe Ser Arg Tyr Ala Arg [SEQ ID NO:4]

corresponding to amino acid residues 13–22 of SEQ ID NO:1. This MNTF fragment includes most of the "WMLSAFS" domain as well as the entire FSRYAR domain. The 10mer was at least as effective the full-length MNTF 33mer at stimulating motor neuron/neuroblastoma cells in vitro at concentrations as low as 0.01 µg/ml.

11-mer

In another preferred embodiment, there is provided a peptide having the following amino acid sequence:
FSRYARCLAEG
Phe-Ser-Arg-Tyr-Ala-Arg-Cys-Leu-Ala-Glu-Gly [SEQ ID NO:5]

corresponding to amino acid residues 17–27 of SEQ ID NO:1. This 11-mer contains the FSRYAR domain and was also found to be sufficient to increase cell proliferation of motor neuron/neuroblastoma cells.

13-mer

In another preferred embodiment, there is provided a peptide having the following amino acid sequence:
CWMLSAFSRYARC
Cys Trp Met Leu Ser Ala Phe Ser Arg Tyr Ala Arg Cys [SEQ ID NO:6]

corresponding to amino acid residues 11 to 23 of SEQ ID NO:1. This 13-mer contains both WMLSAFS and FSRYAR domains and was also found to be sufficient to increase cell proliferation of motor neuron/neuroblastoma cells. However, a cyclized version of the 13-mer was not as effective at stimulating cell proliferation in vitro.

21-mer

In another preferred embodiment, there is provided a peptide having the following amino acid sequence:
MLSAFSRYARCLAEGHDGPTQ
Met Leu Ser Ala Phe Ser Arg Tyr Ala Arg Cys, Leu Ala Glu Gly His Asp Gly Pro Thr Gln [SEQ ID NO:7]

corresponding to amino acid residues 13 to 33 of SEQ ID NO:1. This 21-mer contains most of the "WMLSAFS" domain as well as the entire FSRYAR domain and was also found to be sufficient to increase cell proliferation of motor neuron/neuroblastoma cells.

MNTF Peptide Analogues

It is to be understood that within the scope of the present invention are peptide analogues as described and identified herein in which one or more amino acids are substituted with other amino acids. In a preferred alternative, the motoneuronotrophic factor peptide analogue contains one or more conservative amino acid substitutions to a fragment of seven to 32 consecutive amino acid residues of SEQ ID NO:1.

An MNTF peptide analogue within the scope of this invention can be an altered form of an MNTF1 peptide providing generally of course that the essential activity of the peptide remains substantially unchanged. As used herein, the term "altered form" refers to a peptide that has been treated to change its naturally occurring structure. An altered form can be prepared, for example, by covalent modification of an MNTF1 peptide fragment, by crosslinking MNTF1 peptide fragment to an insoluble support matrix, or by crosslinking MNTF1 peptide fragment to a carrier protein.

An MNTF1 peptide analogue within the scope of this invention can be a peptide fragment that is antigenically related to an MNTF1 peptide fragment. Two peptides, which are antigenically related display immunological cross-reactivity. For example, antibodies to the first peptide also recognize the second peptide.

An MNTF1 peptide analogue within the scope of this invention can be a fusion protein containing a MNTF1 peptide fragment attached to a heterologous protein. A heterologous protein has an amino acid sequence not substantially similar to the MNTF1 peptide fragment. The heterologous protein can be fused to the N-terminus or C-terminus of the MNTF1 peptide fragment. Fusion proteins can include, but are not limited to, poly-His fusions, MYC-tagged fusions, Ig fusions and enzymatic fusion proteins, for example beta-galactosidase fusions. Such fusion proteins, particularly poly-His fusions, can facilitate the purification of recombinant MNTF1 peptide fragments.

Peptidomimetics of WMLSAFS and/or FSRYAR domain peptide(s) are also provided by the present invention, and can act as drugs for the modulation of neuronal cell viability and growth by, for example, blocking the function of proteins comprising the WMLSAFS and/or FSRYAR domain(s). Peptidomimetics are commonly understood in the pharmaceutical industry to include non-peptide drugs having properties analogous to those of those of the mimicked peptide. The principles and practices of peptidomimetic design are known in the art and are described, for example, in Fauchere J., Adv. Drug Res. 15: 29 (1986); and Evans et al., J. Med. Chem. 30: 1229 (1987).

Peptidomimetics which bear structural similarity to therapeutically useful peptides may be used to produce an equivalent therapeutic or prophylactic effect. Typically, such peptidomimetics have one or more peptide linkages optionally replaced by a linkage, which may convert desirable properties such as resistance to chemical breakdown in vivo. Such linkages may include —$CH_2NH$—, —$CH_2S$—, —$CH_2$—$CH_2$—, —CH=CH—, —$COCH_2$—, —CH(OH) $CH_2$—, and —$CH_2SO$—. Peptidomimetics may exhibit enhanced pharmacological properties (biological half life, absorption rates, etc.), different specificity, increased stability, production economies, lessened antigenicity and the like which makes their use as therapeutics particularly desirable.

The rational design of WMLSAFS and/or FSRYAR domain mimetics or binding molecules, based on modeled (or experimentally determined) peptide structure, may be carried out by those of skill, using known methods of rational drug design. The goal of rational drug design is to produce structural analogs of biologically active polypeptides or target compounds. By creating such analogs, it is possible to fashion drugs, which are more active or stable than the natural molecules, which have different susceptibility to alteration or which may affect the function of various other molecules. In one approach, one would generate a three-dimensional structure for a target molecule, or a fragment thereof. This could be accomplished by x-ray crystallography, computer modeling or by a combination of both approaches.

Methods of Making

It is understood that an MNTF peptide composition of the present invention may be made by a method that is well known in the art, including but not limited to chemical synthesis by solid phase synthesis and purification away from the other products of the chemical reactions by HPLC, or production by the expression of a nucleic acid sequence (e.g., a DNA sequence) encoding a peptide or polypeptide comprising an MNTF peptide of the present invention in an in vitro translation system or in a living cell. Preferably the MNTF peptide of the composition is isolated and extensively dialyzed to remove one or more undesired small molecular weight molecules and/or lyophilized for more ready formulation into a desired vehicle. It is further understood that additional amino acids, mutations, chemical modification and such like, if any, that are made in a MNTF peptide component will preferably not substantially interfere with receptor recognition of the MNTF docking sequence.

A peptide or polypeptide corresponding to one or more fragments of MNTF1 of the present invention should generally be at least five or six amino acid residues in length, and may contain up to about 7, about 8, about 9, about 10, about 11, about 12, about 13, about 15, about 20 or about 30 residues or so. A peptide sequence may be synthesized by methods known to those of ordinary skill in the art, such as, for example, peptide synthesis using automated peptide synthesis machines, such as those available from Applied Biosystems (Foster City, Calif.). The invention further provides the synthesis and use of cyclic peptides such as those derived from (SEQ ID NO:1) and (SEQ ID NO:6) as shown in Table 1 below.

Covalent modifications can be introduced into a peptide by reacting targeted amino acid residues with an organic derivatizing agent that is capable of reacting with selected side chains or terminal residues. Covalent modification of polypeptides using organic derivatizing agents is well known to those of skill in the art. For example, cysteinyl residues can be reacted with α-haloacetates (and corresponding amines), such as chloroacetic acid or chloroacetamide, to give carboxymethyl or carboxyamidomethyl derivatives. Histidyl residues can be derivatized by reaction with diethylpyrocarbonate at pH 5.5–7.0, or with para-bromophenacyl bromide at pH 6 in 1 M sodium cacodylate. Lysinyl and amino terminal residues can be reacted with succinic or other carboxylic acid anhydrides. Arginyl residues can be modified by reaction with one or several conventional reagents, among them phenylglyoxal, 2,3-butanedione, 1,2-cyclohexanedione, and ninhydrin. Spectral labels can be introduced into tyrosyl residues by reaction with aromatic diazonium compounds or tetranitromethane; most commonly, N-acetylimidizol and tetranitromethane are used to form O-acetyl tyrosyl species and 3-nitro derivatives, respectively. Carboxyl side groups (aspartyl or glutamyl) can be selectively modified by reaction with carbodiimides (R'—N=C=N—R') such as 1-cyclohexyl-3-(2-morpholinyl-(4-ethyl) carbodiimide or 1-ethyl-3 (4 azonia 4,4-dimethylpentyl) carbodiimide. Furthermore, aspartyl and glutamyl residues are converted to asparaginyl and glutaminyl residues by reaction with ammonium ions. Glutaminyl and asparaginyl residues can be deamidated to the corresponding glutamyl and aspartyl residues. Other modifications include hydroxylation of proline and lysine, phosphorylation of hydroxyl groups of seryl or threonyl residues, methylation of the α-amino groups of lysine, arginine, and histidine side chains (T. E. Creighton, 1983, Proteins: Structure and Molecule Properties, W.H. Freeman & Co., San Francisco, pp. 79–86), acetylation of the N-terminal amine, and, in some instances, amidation of the C-terminal carboxyl groups.

The invention further provides the novel MNTF peptide analogues for use in assays and kits for assays, either in the free form or linked to a carrier molecule such as a protein or a solid particle, as well as modified peptides linked to a label or tracer e.g. biotin or fluorescein isothiocyanate.

Crosslinking of MNTF1 peptide fragment to a water-insoluble support matrix can be performed with bifunctional agents well known in the art including 1,1-bis(diazoacetyl)-2-phenylethane, glutaraldehyde, N-hydroxysuccinimide esters, for example, esters with 4-azidosalicylic acid, homo-bifunctional imidoesters, including disuccinimidyl esters such as 3,3'-dithiobis(succinimidylpropionate), and bifunctional maleimides such as bis-N-maleimido-1,8-octane. Bifunctional agents such as methyl-3-[(p-azidophenyl) dithio]propioimidate yield photoactivatable intermediates that are capable of forming crosslinks in the presence of light. Alternatively, reactive water-insoluble matrices such as cyanogen bromide-activated carbohydrates can be employed for protein immobilization.

Crosslinking of an MNTF1 peptide fragment to a second protein, including a second MNTF1 peptide fragment, can be performed using the bifunctional reagents described herein. In another alternative, there is inserted a spacer, for example a dithiol group or a diamino group or multiples of amino acid residues, e.g. glycine. The spacer may also be a homo- or hetero-bifunctional crosslinker, for example the heterobifunctional crosslinker N-(4-carboxy-cyclohexyl-methyl)-maleimide.

Antibodies to an MNTF1 peptide fragment can be prepared by methods that are well known in the art (see, e.g., Antibodies: A Laboratory Manual, Cold Spring Harbor Laboratory, 1988). A wide range of animal species can be used for the production of antibodies. Typically the animal used for production of antibodies is a rabbit, a mouse, a rat, a hamster, a guinea pig and/or a goat. Antiserum can be used as is for various applications. Alternatively, the desired antibody fraction can be purified by well-known methods such as affinity chromatography using another antibody, protein A and protein G chromatography, and chromatography using a peptide bound to a solid matrix.

Immunological cross-reactivity can be determined using standard immunological assays well known in the art. For example enzyme linked immunosorbent assay (ELISA) can be performed by immobilizing an MNTF1 peptide analogue onto the well surface of a microtiter plate, then contacting the immobilized MNTF1 peptide analogue with antibodies to an MNTF1 peptide fragment. After washing to remove unbound and non-specifically bound antibody, the bound antibody can be detected. Where the initial antibodies are linked to a detectable label, the bound antibody can be detected directly. Alternatively, the bound antibody can be detected using a second antibody that has binding affinity for the first antibody, with the second antibody being linked to a detectable label.

Longer peptides or polypeptides, e.g a fusion protein, can be produced by standard recombinant DNA techniques. For example, a DNA fragment encoding a MNTF1 peptide fragment can be cloned in a commercially available expression vector that already contains a heterologous protein, with the result being MNTF1 peptide fragment fused in-frame to the heterologous protein.

In certain embodiments, a nucleic acid encoding an MNTF peptide and/or a component described herein may be used, for example, to produce a peptide in vitro or in vivo for the various compositions and methods of the present invention. For example, in certain embodiments, a nucleic acid encoding an MNTF peptide is a component of, for example, a vector in a recombinant cell. The nucleic acid may be expressed to produce a peptide or polypeptide comprising an MNTF peptide sequence. The peptide or polypeptide may be secreted from the cell, or as part of or within the cell.

Compositions

Pharmaceutical compositions in accordance with the present invention preferably comprise one or more of the MNTF1 peptide analogues of the present invention together with a pharmaceutically acceptable diluent and/or carrier. Suitable carriers/diluents are well known in the art and include saline or other sterile aqueous media, optionally including additional components such as buffer salts and preservatives, or sugars, starches, salts or mixtures thereof.

The pharmacological compositions of the present invention are prepared in conventional dosage unit forms by the incorporation of one or more of the MNTF peptide analogues with an inert, non-toxic pharmaceutical "carrier" moiety according to accepted methodologies, in a non-toxic concentration sufficient to produce the desired physiological activity in a mammal and, in particular, a human subject. Preferably, the composition contains the active ingredient in a biologically active, but non-toxic, concentration, e.g., a concentration of approximately 5 ng to 50 mg of active ingredient per dosage unit (e.g., per kg subject body weight). The concentration utilized will be dependent upon such factors as the overall specific biological activity of the ingredient, specific biological activity desired, as well as the condition and body weight of the subject.

The pharmaceutical carrier or vehicle employed may be, for example, a solid or liquid and a variety of pharmaceutical forms may be employed. Thus, when a solid carrier is utilized, the preparation may be plain milled, micronized in oil, tabulated, placed in a hard gelatin or enterically-coated capsule in micronized powder or pellet form, or in the form of a troche, lozenge, or suppository. The solid carrier, containing the MNTF peptide analogue, can also be ground up prior to use.

When utilized in a liquid carrier, the preparation may be in the form of a liquid, such as an ampule, or as an aqueous or non-aqueous liquid suspension. For topical administration, the active ingredient may be formulated using bland, moisturizing bases, such as ointments or creams. Examples of suitable ointment bases include, but are not limited to, petrolatum plus volatile silicones, lanolin, and water in oil emulsions such as Eucerin® (Beiersdorf). Examples of suitable cream bases include, but are limited to, Nivea Cream® (Beiersdorf), cold cream (USP), Purpose Cream® (Johnson & Johnson), hydrophilic ointment (USP), and Lubriderm® (Warner-Lambert).

Additionally, with respect to the present invention, the active ingredient may be applied internally at or near the site of the affected motoneuron. For example, a solid or gelled medium which is sufficiently permeable to allow the release of the active ingredient, preferably in a timed-release manner, may be utilized for such internal application. Examples of such gels include, but are not limited to, hydrogels such as polyacrylamide, agarose, gelatin, alginate, or other polysaccharide gums. Furthermore, the active ingredient may be imbedded in a solid material, such as filter paper, which is capable of absorbing and subsequently releasing the active ingredient, at the appropriate time and location.

MNTF peptides according to the present invention may be provided for use in any suitable form appropriate to the protocol of administration and/or the needs of a patient.

Apart from the pharmaceutically acceptable compositions referred to above, the peptides may for example be provided, either singly or in combination, in lyophilized or freeze dried solid forms.

Methods of Use

Truncated MNTF molecules comprising the WMLSAFS and/or FSRYAR domain(s), such as SEQ ID NO: 2, SEQ ID NO: 3, SEQ ID NO: 4, SEQ ID NO: 5, SEQ ID NO: 6, SEQ ID NO: 7, as well as other small peptide derivatives that constitute a "minimal" WMLSAFS and/or FSRYAR domain, are demonstrated herein to retain the neurotrophic and neurotropic function exhibited by the MNTF1–F6 33-mer. These MNTF peptide analogues induce cell growth in neuronal cell lines by providing the same biological signal produced by high level expression of MNTF1 (which has been shown to selectively promote motor neuron viability and axonal regeneration in vitro and in vivo). Such agents comprise a novel class of neurotrophic and neurotropic drug.

MNTF1 and/or its peptide analogues promote the survival of mammalian motor neurons in vitro and stimulate proliferation of the VSC4.1 cell line, a hybrid between motor neurons and neuroblastoma cells. Accordingly, the present invention provides for the use of an MNTF peptide analogue as a growth factor/supplement for neuronal cell cultures, including a method for promoting the survival of primary cultures of neurons or stimulating cell proliferation of neuronal cell lines, by cultivating neuronal cells in vitro with an effective amount of a MNTF peptide analogue as defined above.

In vivo administration of MNTF1 to surgically axotomized rat peripheral nerves resulted in a markedly higher percentage of surviving motor neurons than untreated controls, which could be blocked by co-administration of anti-MNTF1 monoclonal antibody. Further beneficial effects of MNTF1 were demonstrated in rats subjected to spinal cord hemi-section, repaired by a peripheral nerve autograft and implanted with MNTF1-containing gel sections in close proximity to the nerve graft junctions with spinal cord. MNTF1 treated animals exhibited greater numbers of surviving motor neurons as well as improved recovery of motor and sensory function. Moreover, as demonstrated in the femoral nerve model, described in greater detail in the examples below, treatment of transected and sutured rat femoral nerves with MNTF1 peptides resulted in significant increases in correct projections of motor neurons to target muscle tissues in vivo, as well as marked reductions in the number of incorrect projections to skin. Thus the MNTF1 peptides of the present invention are capable of promoting selective reinnervation of target muscle tissue.

Accordingly, the present invention provides therapeutic or prophylactic methods for treating damaged or diseased motoneurons, or pathological conditions, such as neurodegenerative disease, and the like, which are accomplished by the administration of an effective amount of a therapeutic agent capable of specifically promoting neuronal cell viability and/or axonal regeneration. Therapeutic or prophylactic indications can include treatment of (prevention and/or reduction of the severity) of neurological conditions including:

a) acute, subacute, or chronic injury to the nervous system, including traumatic injury, chemical injury, vascular injury and deficits (such as the ischemia resulting from stroke), together with infectious/inflammatory and tumor-induced injury, b) aging of the nervous system, c) chronic immunological diseases of the nervous system or affecting the nervous system, including multiple sclerosis, d) chronic neurodegenerative diseases of the nervous system and musculoskeletal disorders including hereditary motoneuron diseases such as amyotrophic lateral sclerosis, spinal muscular atrophy;

e) peripheral nerve, spinal cord and head injuries, f) peripheral neuropathy, diabetic peripheral neuropathy, peripheral neuropathy resulting from AIDS, peripheral neuropathy resulting from radiation treatment for cancer, Administration of MNTF1 has also been associated with reduced scar formation and inflammation following surgical incision and repair of rat spinal cords. Moreover, recombinant MNTF1 was associated with a marked reduction in the growth of non-neuronal cells, e.g. glial cells and fibroblasts, in spinal cord explants in vitro. Thus in another aspect the present invention provides novel MNTF peptide analogues and compositions consisting of or containing them for use as antiproliferative agents, particularly anti-inflammatory or antifibrotic agents. Moreover the present invention also provides a method of inhibiting proliferation and or migration of non-neuronal cells, particularly fibroblasts and inflammatory cells, by administration of an MNTF peptide analog to a cell culture, more particularly hyperproliferative scar tissue or keloid fibroblasts, or to the site of injury and/or scarring in a mammalian host. The invention also provides such novel MNTF peptide analogues and compositions consisting of or containing them for use in wound healing and cosmetic applications.

The MNTFs of the present invention can thus be readily utilized in pharmacological applications. In vivo applications include administration of the factors to mammalian subjects and, in particular, to human subjects. Any mode of administration that results in the delivery of the therapeutic agent to the desired cell is contemplated as within the scope of the present invention. The site of administration and cells will be selected by one of ordinary skill in the art based upon an understanding of the particular disorder being treated. Principles of pharmaceutical dosage and drug delivery are known and are described, for example, in Ansel, H. C. and Popovich, N. G., Pharmaceutical Dosage Forms and Drug Delivery Systems, 5th Edition, Lea & Febiger, Publisher, Philadelphia, Pa. (1990).

Administration of peptides of the invention in any of the methods described herein may be via any suitable protocol. The particular mode of administration can also be readily selected by one of ordinary skill in the art and can include, for example, oral, intravenous, subcutaneous, intramuscular, etc. with the preferred mode being topical application at or near the affected site. In addition, the dosage, dosage frequency, and length of course of treatment, can be determined and optimized by one of ordinary skill in the art depending upon the particular degenerative disorder being treated. Such administration of peptides of the invention is in such an amount as to give the desired effective result of the peptide's activity at the intended site. Thus, a quantity which constitutes an "effective" amount may depend upon various parameters, such as body weight of the patient, degree of activity required, intended site of activity, severity of the condition to be treated or prevented, all of which will be well understood and appreciated by persons skilled in the art.

As used herein, the terms "administer" includes applying the purified peptide to neuronal or non-neuronal cells or tissues sufficiently proximal to the affected site such that the polypeptide is effective at promoting the survival of mammalian neurons and/or reduced proliferation or infiltration of non-neuronal cells, such as fibroblasts or inflammatory cells.

In yet a further aspect, the present invention provides the above-defined MNTF peptide analogues, particularly the linked peptide analogues of the invention, for use as immunogens for the production of polyclonal and monoclonal antibodies to MNTF1, especially for diagnostic, prognostic and therapeutic uses. Such methods of production of polyclonal and monoclonal antibodies are also within the scope of the invention.

EXAMPLES

The invention may be appreciated in certain aspects with reference to the following examples, offered by way of illustration, not by way of limitation.

Materials, reagents and the like to which reference is made in the following examples are obtainable from commercial sources, unless otherwise noted.

Example 1

Production Procedure for MNTF Bio Peptides

This example shows how to manufacture MNTF peptides
1.) Synthesis—All peptides were synthesized via t-Boc chemistry using a CS536 Automated Peptide Synthesizer (CS Bio Inc.). Deprotection of the Boc groups was performed using 40% TFA(trifluoracetic acid) in Methylene Chloride. Coupling reactions were performed for a period of 2 hours using Diiosopropylcarbodiimide(DIC). Kaiser tests (ninhydrin based) were performed at the completion of each coupling cycle to check coupling efficiency.

2.) The peptide was then cleaved from the resin using HF (hydrogen fluoride). After the HF reaction, the peptide was then extracted with TFA. The extracted material was then lyophilized to obtain an accurate weight prior to the purification process.

3.) The crude peptide was then loaded on to an HPLC column packed with reverse phase C18 resin. A gradient was run from Buffer A (0.1% TFA in $H_2O$) to Buffer B(60% Acetonitrile in 0.1% TFA/$H_2O$) and fractions of the eluant were collected. The resulting fractions were analyzed by analytical HPLC and fractions containing correct material with a purity of >95% were pooled and lyophilized.

4.) The peptide was then frozen and lyophilized. After the final lyophilization process, the peptide was checked at CS Bio for HPLC purity and mass spectral conformation.

Example 2

IN VITRO Assay of MNTF Derivatives

Introduction

Studies of the function of motor neurons have been enhanced by the development of cell lines that mimic their function. Several neuronal cell lines including sensory-F11, motor-VSC 4.1, and adrenergic-N1E-115 neuroblastoma cells, as well as Schwann cells have been used as neuronal models for in vitro detection of programmed cell death (PCD) or apoptosis and/or inhibitory effects of sera from amyotrophic lateral sclerosis patients or diabetic patients with neuropathy on growth, proliferation, and differentiation. In particular, the VSC4.1 cell line, a hybrid between motor neurons and neuroblastoma cells developed by Dr. Stanley Appel, has been used extensively in studies of the pathogenesis of amyotrophic lateral sclerosis (Kimura F, et al. *Annals of Neurology* 35:164–171, 1994; Smith R G, et al. *Proc Natl Acad Sci U.S.A* 91:3393–3397, 1994; Alexianu M E, et al. *J Neurochem* 63:2365–2368, 1994; Appel et al. *Clin Neurosci* 3:368–374, 1995–1996; and Mosier D R, et al. *Ann Neurol* 37:102–109, 1995, which are all incorporated herein by reference). Thus, VSC4.1 cells have been useful in examining the pathogenesis of motor neuropathies and for examination of factors that may protect the cells from damage in the face of systemic factors.

This example shows that certain truncated MNTF peptides stimulate the proliferation of VSC4.1 cells in a manner comparable to the MNTF1 33-mer. These proliferative effects may be related to the ability of MNTF to block or reverse motor nerve loss.

Methods

Studies of proliferation were performed in 96 well plates utilizing a cell proliferation assay kit from Roche Diagnostics GmbH (Mannheim, Germany). VSC4.1 cells, a motor neuron/neuroblastoma cell hybrid, were cultured in DMEM with 2% FBS containing either no MNTF or a dose range of MNTF from $10^{-8}$ to $10^{-5}$ g/ml. Each treatment was applied in triplicate wells. The cells were cultured for 21 hours and 5-bromo-2'-deoxyuridine (BrdU) from the assay kit was added to each well. After BrdU labeling for 3 hours, the cells were washed, fixed and dried. The cells were then fixed and the DNA denatured to improve access for the subsequent antibody binding. POD-labeled mouse monoclonal anti-BrdU antibody from the assay kit was applied for 2 hours, followed by a wash. The assay was quantitated by adding the colorimetric assay solution (tetramethyl benzidine) and reading at 450 nm on a Wallac Vector 2 plate reader. Cells in the treatment groups were quantitated by comparing to wells plated with a gradient of cells from 0 to 20,000 cells/well on the same plate. Data is expressed as % of control to allow for variability from plate to plate.

Results

The following table summarizes the results of three sets of cell proliferation assays conducted on separate occasions (10-27-02, 3-28-03 and 8-4-03).

TABLE 1

| MNTF | | Lot #** | M.W. | Grade* | Biological Function |
|---|---|---|---|---|---|
| | Oct. 27, 2002 | | | | |
| 33mer | SEQ ID NO: 1 | 16064A1 | 3706 | Rg, L | Effective. OD at 10 ug/ml. |
| 33mer | SEQ ID NO: 1 | 16062A2 | 3706 | Rg, C | Limited Efficacy. |
| 33mer | SEQ ID NO: 1 | CS1456 | 3706 | GLPg, L | Effective. OD at 0.1 ug/ml. |
| 13mer | SEO ID NO: 6 | 43426 | 1594 | Rg, C | Limited Efficacy. |
| 7mer | SEQ ID NO: 3 | 43425 | 841 | Rg, L | Effective. OD at 1 ug/ml |
| 6mer | SEQ ID NO: 2 | 43427 | 799 | Rg, L | Effective. OD at 10 ug/ml. |
| 11mer | SEQ ID NO: 5 | 43428 | 1273 | Rg, L | Effective. OD at 10 ug/ml. |
| | Mar. 28, 2003 | | | | |
| 33mer | SEQ ID NO: 1 | 16064A1 | 3706 | Rg, L | Effective. OD at 100 ug/ml. |
| 33mer | SEQ ID NO: 1 | CS-C118=CS1456 | 3706 | GLPg, L | Effective. OD at 10 ug/ml. |
| 13mer | SEQ ID NO: 6 | CS-C171=CS1510 | 1594 | GLPg, L | Effective. OD at 0.1 ug/ml. |
| 7mer | SEQ ID NO: 3 | CS-C173=CS1511 | 841 | GLPg, L | Effective. OD at 100 ug/ml. |
| 6mer | SEQ ID NO: 2 | CS-C158=CS1507 | 799 | GLPg, L | Effective. OD at 1 ug/ml. |
| 11mer | SEQ ID NO: 5 | CS-C172=CS1509 | 1273 | GLPg, L | Effective. OD at 1 ug/ml. |
| | Aug. 4, 2003 | | | | |
| 33mer | SEQ ID NO: 1 | CS1456=CS-C297 | 3706 | GLPg, L | Effective. OD at 0.01 ug/ml. |
| 21mer | SEQ ID NO: 7 | CS1616=CS-C382 | 2311 | GLPg, L | Effective. OD at 0.1 ug/ml. |
| 10mer | SEQ ID NO: 4 | CS1597=CS-C337 | 1201 | GLPg, L | Effective. OD at 0.01 ug/ml. |

*Rg = research grade (~70% purity), GLPg = GLP grade (90–99.8% purity), L = linear peptide, C = Cyclized peptide, OD = optimal dose
**CS-C### = Batch number of a manufacturing process catalog number CS#### of CS Bio Inc., the GMP product manufacturer. Lot numbers without "CS" are research grade products from Genemed Synthesis.

Referring to the earliest studies listed in Table 1, and shown in FIG. 2, MNTF 33mer (research grade) alone applied to the cultures resulted maximally in a 31.7% increase in cell proliferation of VSC4.1 motor neuron/neuroblastoma hybrid cells at a dose of 10 µg/ml. Higher doses were not tested. Cyclized MNTF 33mer was of limited efficacy, stimulating a maximal response of 12.9% albeit at a lower dose than MNTF, 100 ng/ml.

Of the other peptides supplied, the most effective in this assay was the GLP grade MNTF 33mer, which stimulated a maximal response of 34.3%, also at a dose of 100 ng/ml (FIG. 2). Of the other peptides, the MNTF 6mer and 11mer were comparably effective (FIG. 2), achieving maximal responses of 35.1% and 32.2%, respectively. These responses were also seen at the highest tested dose, 10 µg/ml. The MNTF 7mer was somewhat less effective with a maximal effect of 25.1% at a dose of 1 µg/ml (FIG. 2), although this peptide had a broader active dose range than the other preparations. The cyclized MNTF 13mer peptide was the least effective of all peptides tested, with a maximal effect of 17.3% at 1 µg/ml (FIG. 2). Moreover, at higher doses the cyclized MNTF 13mer peptide appeared to inhibit proliferation.

Although the percentage increases reported in these preliminary experiments were not high, this was likely due to the high rate of proliferation of these cells under basal conditions. With that caveat, the MNTF peptide analogues appear to be relatively effective in a dose dependent manner, with the exception of cyclized versions of the peptides. Of the peptides tested, GLP grade 33mer (SEQ ID NO:1) was the most biologically active in this assay, given the high rate of proliferation and the low dose needed for induction. Research grade 6mer (SEQ ID NO:2) and 11mer (SEQ ID NO:5) are comparably effective, not only to each other but also to the MNTF 33mers. The cyclized 13mer (SEQ ID NO:4) was markedly less effective than the other derivative peptides. Moreover, cyclized MNTF 33mer peptide showed very weak proliferative activity at low doses.

Additional cell proliferation assays, conducted essentially as described above, were performed to compare the effects of several GLP grade MNTF peptides.

The MNTF preparations utilized for this assay were:

| | |
|---|---|
| 16064A-1 | 33mer Research Grade |
| CS-C118 | 33mer GLP Grade |
| CS-C158 | 6mer GLP Grade |
| CS-C173 | 7mer GLP Grade |
| CS-C172 | 11mer GLP Grade |
| CS-C171 | 13mer GLP Grade |

Figure 3:
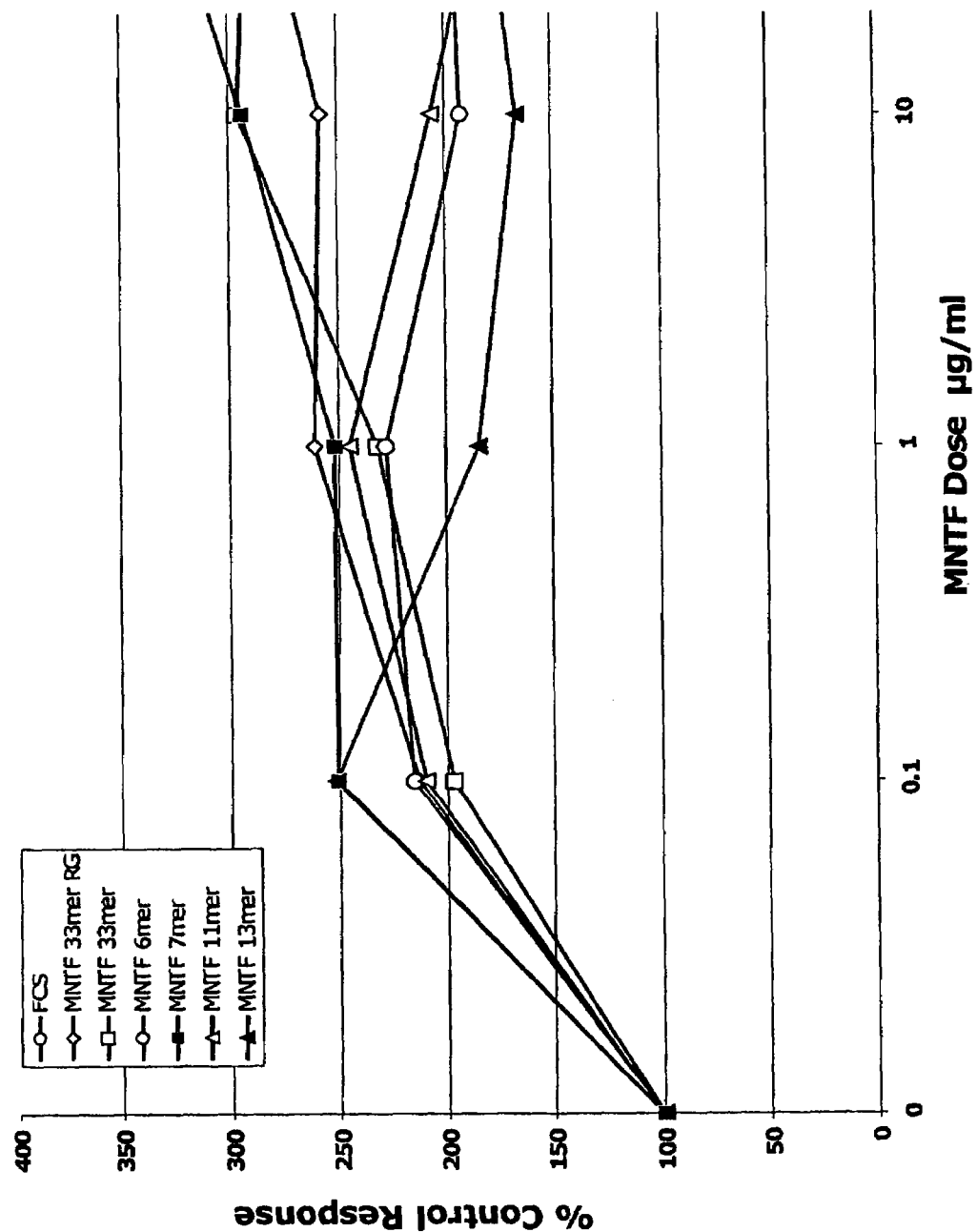
FIG. 3 also shows percent increases in proliferation of VSC4.1 cells by highly purified (GLPg) MNTF1–F6 33mer and its peptide derivatives at various doses.

As shown in Table 1 and FIG. 3, all MNTF peptide preparations exerted proliferative effects on VSC4.1 cells, although to varying degrees. The most potent preparation across the whole dose range was the 7mer, showing a 2.5-fold increase even at the lowest dose applied, while exerting almost a 3.5-fold increase in proliferation at the highest dose. Although the 13mer showed some efficacy at the lowest dose, this effect fell off at higher doses. The two 33mers, showed a steady increase in response with increasing dosage, with the Research Grade 33mer peaking at about a 3-fold increase at the highest dose, while GLPgrade reached a peak 3-fold response at 10 µg/ml with no further increase with increasing dosage. Less robust performers in this set of assays were the 6mer, and the 11mer. Although these preparations stimulated almost a 2.5-fold increase in proliferation at 1 µg/ml, the performance across the whole dose range was not as potent as the other isoforms of MNTF.

In this second round of experiments, the assay overall was more robust, with the most active proliferative agent, the 7mer, producing a 350% increase over controls. Four of six MNTF isoforms provided stimulated VSC4.1 cell proliferation 250% or greater. However, one of these, the 13 mer, did so only at a single dose. The other two MNTF isoforms, i.e., the 6mer and the 11mer, although they did stimulate proliferation, did so less effectively than the others. The relative efficacy would be: 7mer (SEQ ID NO:3)>33mer (SEQ ID NO:1)>>6mer (SEQ ID NO:2), 11mer (SEQ ID NO:5)>13mer (SEQ ID NO:6).

Further cell proliferation studies were performed, essentially as described above, to test the response of the motor neuron/neuroblastoma cells to three new preparations of MNTF. The MNTF preparations utilized for these assays were:

| | |
|---|---|
| 1456 | 33mer |
| 1597 | 10mer |
| 1616 | 21mer |

Figure 4:
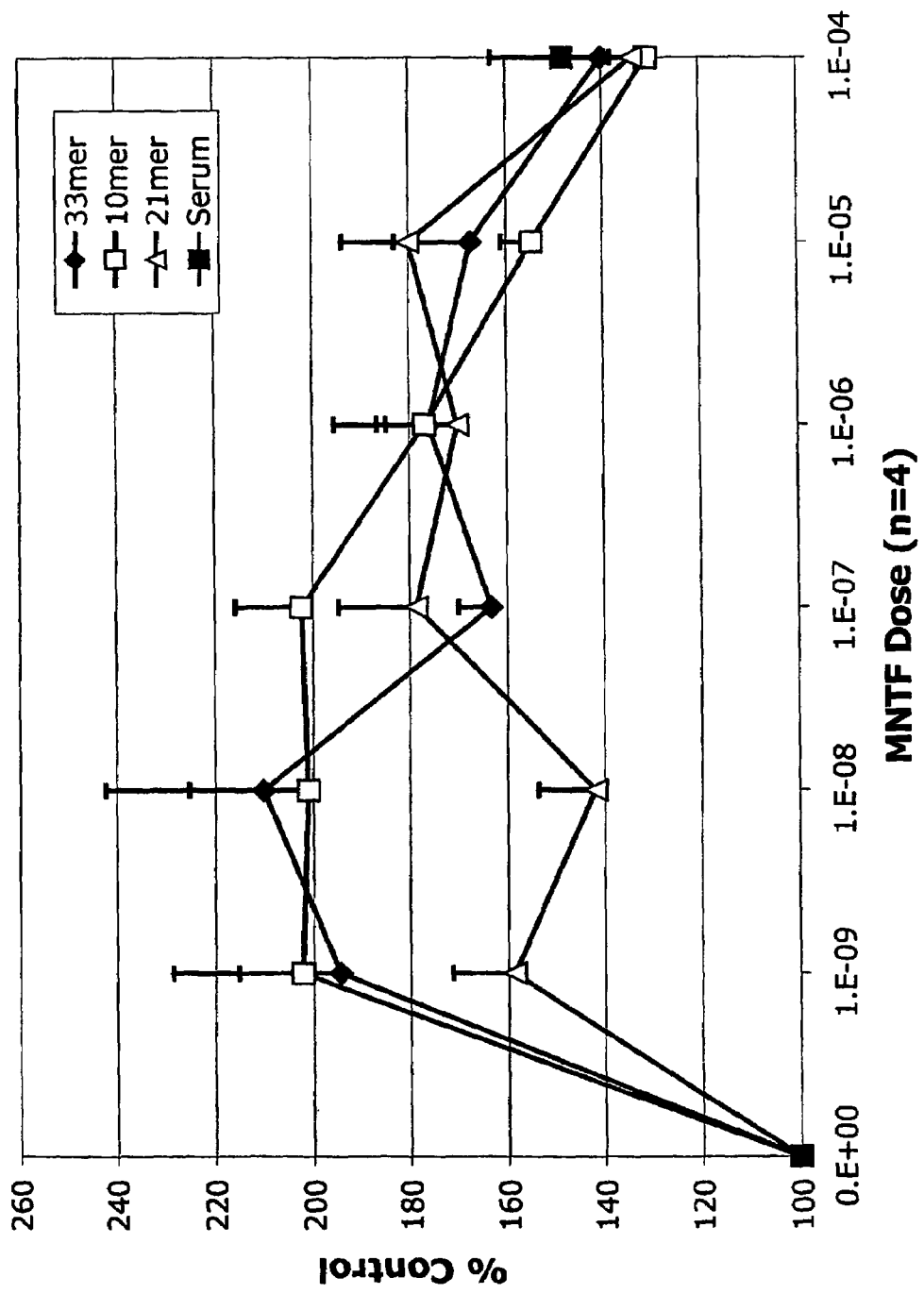
FIG. 4 shows percent increases in proliferation of VSC4.1 cells by MNTF1–F6 33mer and additional peptide derivatives at various doses.

As shown in Table 1 and FIG. 4, all three MNTF isoforms significantly stimulated VSC4.1 cell proliferation (ANOVA, as indicated) when expressed as percentage increase over control. Further, the 10mer, the 21mer and the 33mer significantly ($p<0.05$) stimulated proliferation over control at specific doses. 33mer: $p<0.02$. 10mer: $p<0.001$. 21mer: $p<0.002$.

As in the previous experiments, the assay overall was robust. The most active proliferative agent appeared to be the 10mer, producing approximately a 200% increase over controls at the three lowest doses used ($p<0.005$, ANOVA). All three of these doses were significantly different from control (Tukey-Kramer post-hoc analysis). The 33mer stimulated cell proliferation ($p<0.01$, ANOVA) nearly as well as the 10mer at low doses ($10^{-9}$ and $10^{-8}$ g/ml significant by Tukey-Kramer post-hoc analysis), closely approximating the response to the 10mer at higher doses. While the 21mer significantly stimulated proliferation ($p<0.05$, ANOVA), the increase over controls was about half that of the other two MNTF isoforms and not significantly different at any one dose, although at high doses the responses to all three were similar.

Thus, all three isoforms of MNTF significantly stimulated motor neuron proliferation, although the 10mer (SEQ ID NO:4) and 33mer (SEQ ID NO:1) were clearly superior to the 21mer (SEQ ID NO:7). While these percentage responses seem to be somewhat lower than in the previous assays, this could be due to interassay variability, caused by different activities of different cell passages in culture.

Example 3

In Vivo Assays for Neurotropic Activity

The Femoral Nerve Model

The specificity of motor axon regeneration was investigated in the rat femoral nerve. Proximally, at the site of nerve transection and suture, axons that contribute to both cutaneous and muscle branches intermingle throughout the nerve. As these axons regenerate, they have equal access to neighboring motor and sensory Schwann cell tubes in the distal nerve stump. This assures an element of "choice" at the axonal level. Distally, where the specificity of regeneration is assessed, axons are segregated into terminal cutaneous and muscle branches. Motor axons are normally found only in the muscle branch, so any motor reinnervation of the cutaneous branch represents a pathfinding failure. The specificity of axon regeneration is evaluated by simultaneous application of horseradish peroxidase (HRP) to one distal femoral branch and fluoro-gold (FG) to the other. Motor-axon regeneration is random at 3 weeks, but the number of correct projections to muscle increases dramatically at later times. Many neurons initially contain both tracers, and thus project collaterals to both cutaneous and muscle branches. The number of these double-labeled neurons decreases with time. Motor axon collaterals are thus pruned from the cutaneous branch, increasing the number of correct projections to muscle at the expense of double-labeled neurons. A specific interaction thus occurs between regenerating motor axons and muscle and/or muscle nerve that we have termed Preferential Motor Reinnervation (PMR).

MNTF Pump Experiments

In preliminary experiments we attempted to modify motor axon regeneration in the femoral nerve by pumping MNTF 33mer at $10^{-4}$ M onto the repair site, using an Alzet osmotic pump which discharges for at least 2 weeks. The output of the pump was sewn to muscle adjacent to the nerve repair, so that the nerve wound would be continuously bathed with the factor. Reinnervation of the distal femoral cutaneous and muscle branches was quantified with tracers as described above.

The controls for these preliminary experiments were a group of 10 nerves that underwent routine suture and evaluation after three weeks of regeneration. A mean of 92 motoneurons projected correctly to muscle at three weeks, while a larger number (mean=117) projected incorrectly to skin. However, MNTF 33mer treatment in three animals more than doubled the number of correct projections (mean=210) while dramatically reducing the number incorrect projections to skin (mean=31). These differences were highly significant in spite of the small number of animals tested.

In a follow-up experiment MNTF 33mer was administered to eight transected and sutured rat femoral nerves at $10^{-4}$ M, essentially as described above. Controls were a group of six nerves that underwent routine suture with pumps delivering saline but no MNTF. A mean of 100 motoneurons projected correctly in the six controls, whereas a mean of 87 motoneurons projected incorrectly to skin. MNTF treatment once again resulted in a significant increase in correct projections (mean=173) and a marked reduction in the number of incorrect projections to skin (mean=59).

Figure 5:
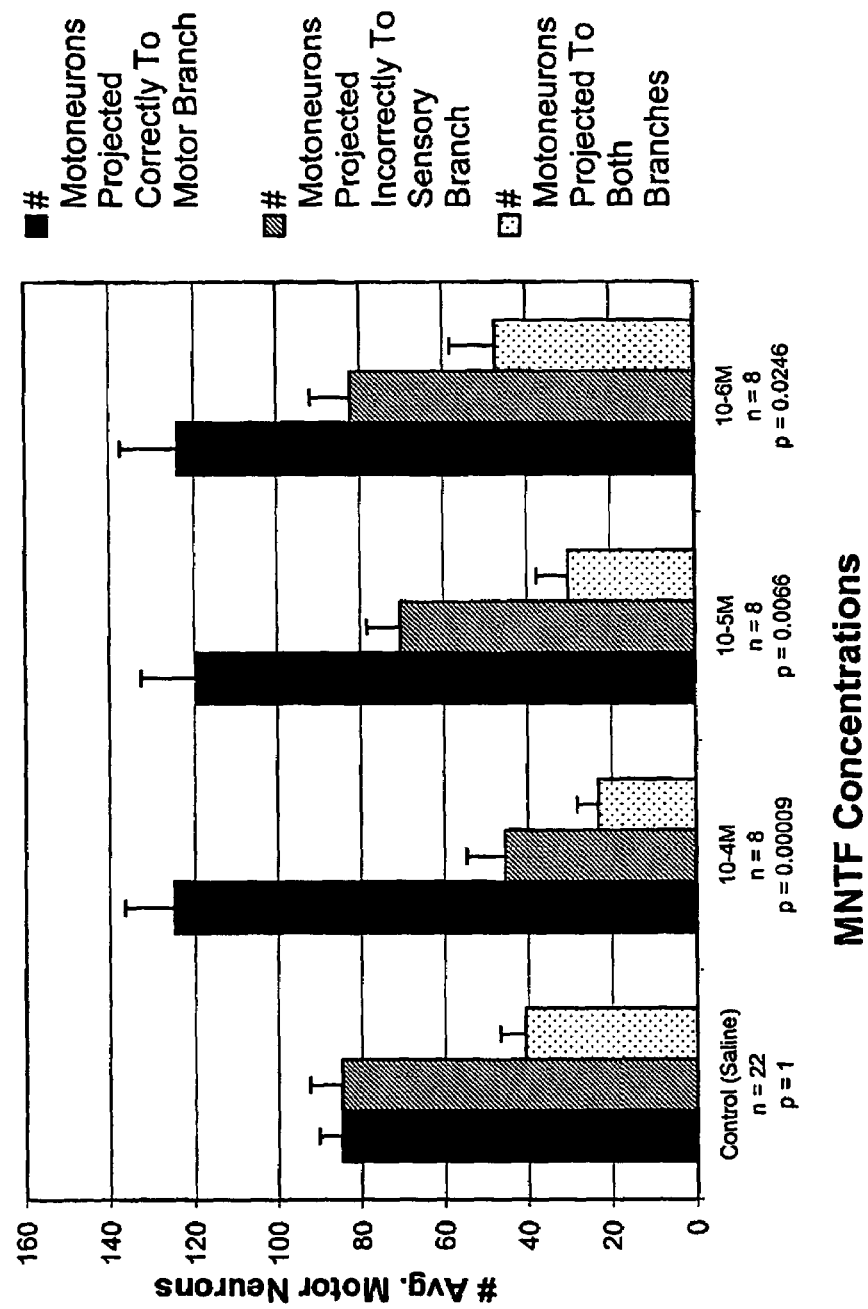
FIG. 5 shows selective reinnervation of target muscle cells by motor neurons treated with MNTF 6mer at various doses.

To determine if a truncated MNTF peptide could be substituted for MNTF 33mer, subsequent experiments were performed, essentially as described above, using the MNTF 6mer FSRYAR, at $10^{-4}$ M (n=8), $10^{-5}$ M (n=8) and $10^{-6}$ M (n=8), with a total of 22 saline controls for comparison. As shown in FIG. 5, treatment with the FSRYAR peptide (SEQ ID NO:2) resulted in significant increases in correct projections at every dose tested as well as marked reductions in the number of incorrect projections to skin. For saline controls, the mean number of cells projecting correctly to muscle was 85, the mean number of incorrect projections to skin was 85 and double-labeled neurons averaged about 41. At the optimal dose of MNTF 6mer ($10^{-4}$ M) the mean number of correct projections increased to 125, incorrect projections were reduced to 46 and double-labeled neurons decreased to 23. Thus the 6mer is capable of promoting selective reinnervation of target muscles in a manner similar to the MNTF1 33mer.

These results demonstrate a dramatic stimulation of regeneration in the rat femoral nerve model using MNTF 33mer as well as the MNTF 6mer peptide, FSRYAR (SEQ ID NO:2). We are unaware of data from other models that show this significant an effect. Most manipulations result in changes of 20–30% at best, while these results show changes of 36% to greater than 100%. Such dramatic results suggest MNTF and it's peptide analogues are among the most potent stimulators of peripheral nerve regeneration currently available.

Example 4

Production of Anti-MNTF Peptide Antibodies and their Use in Immunoassays

Rabbit polyclonal antibodies to the MNTF 33mer as well as the MNTF 6mer, FSRYAR, were produced by Harlan Bioproducts for Sciences, Inc (Indianapolis) following their standard production protocol, which included conjugating the MNTF peptide with KLH before inoculation into rabbits. More MNTF peptides were conjugated to OVA for ELISA in periodic test bleeds to confirm the high titer of antibodies before production bleeds. The polyclonal antibodies were then purified by IgG purification and by Affinity purification.

MNTF Competitive ELISA protocols were developed by Genetel Laboratories, LLC (Madison, Wis.) for detection or measurement of MNTF peptides, e.g., using purified anti-MNTF6mer to detect the ability of unlabeled MNTF peptides, such as a 6mer or 10mer, to compete with their biotinylated counterparts for antibody binding.

Moreover, an MNTF Sandwich ELISA protocol was developed, using anti-MNTF 6mer antibodies to immobilize larger MNTF peptides containing the 6mer epitope, e.g. 21mers and 33mers, which where subsequently detected using biotinylated anti-MNTF 33mer antibody.

Although the present invention has been described in considerable detail with reference to certain preferred versions thereof, other versions are possible. It will be understood that the invention is capable of further modifications and this application is intended to cover any variations, uses, or adoptions of the invention including such departures from the present disclosure as come within known or customary practice within the art to which the invention pertains. Therefore the spirit and scope of the present invention should not be limited to the description of the preferred versions contained herein.

All publications mentioned in this specification are herein incorporated by reference, to the same extent as if each individual publication was specifically and individually indicated to be incorporated by reference.

What is claimed is:

1. A motoneuronotrophic factor peptide analogue selected from the group consisting of SEQ ID NO:2, SEQ ID NO:3, SEQ ID NO:4, SEQ ID NO:5, SEQ ID NO:6, and SEQ ID NO:7.

2. A composition comprising the peptide analogue of claim 1 and a carrier.

3. A motoneuronotrophic factor peptide analogue of claim 1 having a sequence according to SEQ ID NO:2.

4. A motoneuronotrophic factor peptide analogue of claim 1 having a sequence according to SEQ ID NO:3.

5. A motoneuronotrophic factor peptide analogue of claim 1 having a sequence according to SEQ ID NO:4.

6. A motonenronotrophic factor peptide analogue of claim 1 having a sequence according to SEQ ID NO:5.

7. A motoneuronotrophic factor peptide analogue of claim 1 having a sequence according to SEQ ID NO:6.

8. A motoneuronotrophic factor peptide analogue of claim 1 having a sequence according to SEQ ID NO:7.

9. A motoneuronotrophic factor peptide analogue of claim 1 wherein said peptide analogue promotes the outgrowth of mammalian motorneurons.

* * * * *

UNITED STATES PATENT AND TRADEMARK OFFICE
CERTIFICATE OF CORRECTION

| | |
|---|---|
| PATENT NO. | : 7,183,373 B2 |
| APPLICATION NO. | : 10/541343 |
| DATED | : February 27, 2007 |
| INVENTOR(S) | : Raymond Ming Wah Chau et al. |

It is certified that error appears in the above-identified patent and that said Letters Patent is hereby corrected as shown below:

Column 24, line 24 in Claim 6, replace "motonenronotrophic" with --motoneuronotrophic--.

Signed and Sealed this

Eighth Day of May, 2007

JON W. DUDAS
*Director of the United States Patent and Trademark Office*